(12) United States Patent
Martin

(10) Patent No.: US 7,255,797 B2
(45) Date of Patent: Aug. 14, 2007

(54) COMPOSITION INCLUDING POTASSIUM MONOPERSULFATE AND A HALOGEN

(75) Inventor: Perry L. Martin, Yuba City, CA (US)

(73) Assignee: Truox, Inc., McClellan, CA (US)

( * ) Notice: Subject to any disclaimer, the term of this patent is extended or adjusted under 35 U.S.C. 154(b) by 0 days.

(21) Appl. No.: 10/878,899

(22) Filed: Jun. 28, 2004

(65) Prior Publication Data

US 2005/0035065 A1    Feb. 17, 2005

Related U.S. Application Data

(60) Provisional application No. 60/495,083, filed on Aug. 13, 2003.

(51) Int. Cl.
*C02F 1/72* (2006.01)

(52) U.S. Cl. ............... 210/754; 210/758; 210/169; 210/198.1; 423/513

(58) Field of Classification Search ............. 210/753, 210/754, 756, 169, 198.1, 758; 423/513
See application file for complete search history.

(56) References Cited

U.S. PATENT DOCUMENTS

| | | | | |
|---|---|---|---|---|
| 3,671,629 A | * | 6/1972 | Levy et al. ............. | 424/680 |
| 4,880,547 A | * | 11/1989 | Etani ..................... | 210/728 |
| 5,670,059 A | * | 9/1997 | Jones et al. ............ | 210/753 |
| 6,143,184 A | | 11/2000 | Martin et al. .......... | 210/743 |
| 6,149,819 A | | 11/2000 | Martin et al. .......... | 210/743 |
| 6,409,926 B1 | | 6/2002 | Martin ................... | 210/709 |
| 6,432,234 B1 | | 8/2002 | Bathelier ............... | 156/72 |
| 6,620,315 B2 | | 9/2003 | Martin ................... | 210/96.1 |
| 6,623,647 B2 | | 9/2003 | Martin ................... | 210/742 |

* cited by examiner

*Primary Examiner*—Robert Hopkins
(74) *Attorney, Agent, or Firm*—DLA Piper US LLP

(57) ABSTRACT

A product including potassium monopersulfate and a halogen is presented. The product is useful for treatment of aquatic facilities such as swimming pools. While it was known that using a combination of potassium monopersulfate and halogen is effective for sanitizing water, a product that includes both components could not be made because of the incompatibility between the two components. The product overcomes the incompatibility by use of a barrier film between the two components. The barrier film, which includes one or more of inorganic salt, silicate, borosilicate, and organic polymer, is coated onto one of the components prior to being combined with the second component. The product may be extruded and molded into a desired shape and added to the water to be treated, as needed.

46 Claims, No Drawings

COMPOSITION INCLUDING POTASSIUM MONOPERSULFATE AND A HALOGEN

RELATED APPLICATION

This application claims the benefit of U.S. Provisional Application Ser. No. 60/495,083 filed on Aug. 13, 2003 under 35 U.S.C. § 119(e) and incorporates by reference the content of the provisional application in its entirety.

FIELD OF INVENTION

This invention pertains generally to maintenance of aquatic facilities and particularly to sanitizing and/or oxidizing an aquatic facility.

BACKGROUND

Aquatic facilities, such as swimming pools, become contaminated from various components in the environment such as dust, bacteria, and viruses, as well as from waste products produced by the bathers. To ensure that the pools can be enjoyed safely, the pool water is treated to reduce or eliminate chemical oxygen demand (COD) and/or total organic carbon (TOC) in the water. Typically, chlorine or bromine is used to disinfect the water and prevent viruses and bacteria from being transmitted among the bathers. Halogen donor compounds such as chlorine or bromine are also used to sanitize/oxidize waste products produced by the bathers.

To achieve an effective level of antimicrobial and viricidal activity, the oxidation potential of water must be sustained above a threshold value. Sustaining the oxidation potential is an uphill battle, as the oxidation potential is continuously reduced by contaminants' consumption of the sanitizing/oxidizing agent. Studies have confirmed that the effectiveness of chlorine/bromine-based sanitizers is significantly reduced with increased contaminant level. As used herein, the "contaminant" is any substance that reacts with and consumes the sanitizing/oxidizing agent. In swimming pool and other waters, contaminants often come in the form of organic compounds.

Sanitizing water would be relatively easy if the only type of contaminants were inorganic nitrogen waste products (e.g., ammonia, ammonium), as chlorine can convert the ammonia to inert nitrogen gas using the well known breakpoint chlorination process. However, when the water also contains organic nitrogen waste products, the breakpoint chlorination process is significantly impaired. This impairment is at least partly due to the fact that organic nitrogen reacts with the sanitizing agent in a less desirable competing reaction. The competing reaction entails chlorine's reaction with the organic nitrogen to produce a volatile and irritating byproduct known as chloramine ($NH_2Cl$, $NHCl_2$, $NCl_3$, $R_2NCl$, RHNCl, where R represents organic constituent). Because some of the chlorine is turned into chloramines by the organic nitrogen (instead of being turned into inert nitrogen by the inorganic nitrogen), the ability of chlorine (or other halogen)-based sanitizing/oxidizing agent to rid the water of inorganic nitrogen such as mono- and di-chloroamines is significantly impaired.

In applications such as swimming pool water, where both organic and inorganic nitrogen are present, organic nitrogen that forms chloramines competes for chlorine against inorganic nitrogen that forms inert nitrogen. Chloramines accumulate because chlorine is consumed more readily by the organic byproducts than the already partially oxidized chloramines. Accumulation of chloramines is undesirable for a number of reasons. First, chloramines are less effective as oxidizers than chlorine. Second, incomplete oxidation of the Total Organic Carbon (TOC) by reaction with chlorine produces trihalomethane (THM), which are known carcinogens. Furthermore, chloramines and THM induce corrosion of metals and impose mild to severe irritation to bathers' eyes, skin, and respiratory systems.

To control disinfection rates and prevent the accumulation of chloramines, the organic byproducts must be effectively oxidized independently of chlorine, leaving chlorine free to react with the inorganic nitrogen. This way, the chlorine is free to disinfect the water by converting the inorganic nitrogen to inert nitrogen gas. Also, when the TOC is diminished, the potential for formation of THM by reaction between chlorine and the TOC is reduced. Thus, a method and composition for achieving breakpoint chlorination without accumulation of chloramines and formation of incomplete oxidation products is desired.

SUMMARY

The invention includes a water treatment product that effectively reduces the amount of organic and inorganic nitrogen by preventing the accumulation of chloramines. The water treatment product contains a much lower level of irritants than most currently available water treatment products, allowing water treatment even while bathers are in the swimming pool.

In one aspect, the invention is a water treatment composition includes a potassium monopersulfate component, a halogen component including or generating a halogen donor, and a barrier film. The barrier film, which allows the potassium monopersulfate component to be combined with the halogen component, includes one or more of an inorganic salt, silicate, borosilicate, and an organic polymer. In another aspect, the invention is a method of preparing a water treatment composition by providing a potassium monopersulfate component and combining the potassium monopersulfate component with a halogen donor and a barrier film.

In yet another aspect, the invention is a method of treating water by obtaining a solid product containing potassium monopersulfate and a halogen donor, and periodically adding the mixture to a body of water.

The invention is also a method of combining potassium monopersulfate and a halogen donor into a stable product. Potassium monopersulfate and halogen donor(s) were previously not combined because of their incompatibility. The invention includes coating either the potassium monopersulfate with one or more of inorganic salt, silicate, borosilicate, and organic polymer to overcome this incompatibility. After the coating, the halogen donor is added to the coated potassium monopersulfate to form a PMPS-halogen product.

DETAILED DESCRIPTION OF THE PREFERRED EMBODIMENT

Embodiments of the invention are described herein in the context of a swimming pool, and particularly in the context of disinfecting the swimming pool water. However, it is to be understood that the embodiments provided herein are just preferred embodiments, and the scope of the invention is not limited to the applications or the embodiments disclosed herein.

Due to the above-mentioned disadvantages of using a halogen to treat water that contains both organic and inorganic contaminants, potassium monopersulfate ($KHSO_5$, herein referred to as PMPS) is sometimes used with halogen. PMPS is effective at removing TOC and prevents the accumulation of chloramines by allowing them to be oxidized via breakpoint chlorination. Also, unlike chlorine, PMPS does not produce THMs.

However, PMPS has its disadvantages as well. For example, PMPS is usually accompanied by an irritating byproduct, $K_2S_2O_8$ (potassium oxodisulfate). Since bathers can tolerate only a low level of $K_2S_2O_8$, there is naturally a limit to how much PMPS can be added to a body of water. In applications such as swimming pools where the product may come into direct contact with bathers, PMPS is added as part of a shock treatment whereby an entire dosage is spread across the surface of the pool at once. The dosage is limited to 1~2 lb/10,000 gallons per week, depending on the manufacturer. If this limit were to be exceeded, bathers are likely to experience irritation due to accumulation of $K_2S_2O_8$, which has a long half-life. Thus, this dosage cannot be exceeded regardless of how contaminated the pool water is. Moreover, the presence of the irritant means the PMPS treatment must be performed when bathers are not present. Most manufacturers of PMPS-based pool treatment compositions require bathers to wait at least 30 minutes before using the pool after the treatment.

The periodic shock treatment does not provide for sustained disinfection, and undesirably allows the water quality to fall between treatments. Between PMPS treatments, the organic and inorganic nitrogen in the water trigger competing reactions on the sanitizing/oxidizing agent, thereby impairing the disinfection rate. Also, the competing reactions between accumulated organics and nitrogen for the sanitizing/oxidizing agent allow for increased levels of chloramines which impair both water and air quality.

To address these issues, attempts have been made to use PMPS in conjunction with a sanitizing agent, such as a halogen donor. However, a problem with PMPS-and-halogen-based water treatment is that PMPS is not compatible with some of the chlorine/bromine donor products that are most commonly used today (e.g., calcium hypochlorite, dichloro isocyanurate, trichloro-isocyanurate, bromo-chloro-dimethylhydantoin (BCDMH), dibromo-dimethylhydantoin (DBDMH). Thus, to use PMPS with a halogen, sophisticated control and applications technologies are need to be implemented to allow for more frequent feed of PMPS while bathers are present. Due to the incompatibility between PMPS and halogen, these technologies feed the sanitizer and the PMPS separately, and usually independently (e.g., see U.S. Pat. Nos. 6,620,315, 6,409,926, 6,143,184). In these processes, expensive chemical feed and control technology is required along with extensive on-site maintenance and expertise to tune in or optimize the sequencing of the chemicals being fed.

The invention includes a PMPS-halogen product including PMPS and one or more halogen donors. The product overcomes the incompatibility problem between the PMPS and halogen donors by implementing a barrier film between the PMPS and halogen donor(s) which allows the PMPS and the halogen donor to be combined into a stable composition. Preferably, the product uses a PMPS that is substantially free of $K_2S_2O_8$ so that more of the product can be used without posing a health hazard to the bathers. The PMPS-halogen product frees up the halogen to react with inorganic wastes by having PMPS remove organic wastes.

The halogen-PMPS composition contains 1) a halogen component that includes or produces a halogen donor, 2) a PMPS component having the formula $(KHSO_5)_x(KHSO_4)_y(K_2SO_4)_z$, where $x+y+z=1$, $x=0.43-0.75$, $y=0.01-0.40$, $z=0.01-0.40$, and a $K2S2O8<0.5$ wt %, and 3) a barrier film between the PMPS and the halogen components. The weight fractions of the PMPS component, the halogen component, and barrier film are about 4–70.8 wt. %, about 29–95.8 wt. %, and about 0.2–10 wt. %, respectively. This halogen-PMPS composition enhances disinfection rates by sustaining higher oxidation-reduction potential (ORP) values in water that is being treated. Furthermore, this halogen-PMPS composition promotes breakpoint chlorination of organic nitrogen and of inorganic nitrogen in the presence of organic chemical oxygen demand (COD).

In one embodiment, the PMPS component has the formula $(KHSO_5)_x(KHSO_4)_y(K_2SO_4)_z$, where $x+y+z=1$, where $x=0.42-0.64$, $y=0.15-0.40$, and $z=0.15-0.40$. In another embodiment, the PMPS component has the formula $(KHSO_5)_x(KHSO_4)_y(K_2SO_4)_z$, where $x+y+z=1$, where $x=0.48-0.64$, $y=0.15-0.37$, and $z=0.15-0.37$. The process for preparing this PMPS component is described in U.S. Provisional Patent Application Ser. No. 60/505,466, which is incorporated by reference herein in its entirety.

The PMPS component of the PMPS-halogen product is made of about 43 to about 76 wt. % $KHSO_5$, less than about 0.5 wt. % (and preferably less than about 0.2 wt. %) of $K_2S_2O_8$, and sometimes also alkali magnesium salt. Depending on the embodiment, there may be no alkali magnesium salt in the product. The alkali magnesium salt comprises one or more of $Mg(OH)_2$, $MgCO_3$, $Mg(HCO_3)_2$, $MgO$, $(MgCO_3)_4$—$Mg(OH)_2$-$5H_2O$, $CaMg(CO_3)_2$, $MgO$—$CaO$, $Ca(OH)_2$—$MgO$ or combinations thereof.

The halogen component is a substance that includes or generates a halogen donor, such as one or more of calcium hypochlorite, trichloroisocyanurate, dichloroisocyanurate, lithium hypochlorite, dibromo-dimethylhydantoin, bromo-chloro-dimethylhydantoin, sodium bromide, and sodium chloride.

The barrier film, which may be an inorganic salt, silicate, borosilicate, an organic polymer, or any combination thereof, allows the halogen donor and the PMPS composition to be combined. The inorganic salt may be one or more of sodium, potassium, magnesium, calcium, or a combination thereof, combined with one or more of carbonate, bicarbonate, hydroxide, oxide, silicate, borate, or combinations thereof. The silicate may be sodium, potassium, lithium, silicate, borosilicate, or a combination thereof. The organic polymer comprises chitin, chitosan, polymaleic acid, phosphinocarboxylic acid, carboxylate-sulfonate copolymer, a carboxylate-sulfonate terpolymer, or a combination thereof. The carboxylate component of the carboxylate-sulfonate copolymer or the carboxylate-sulfonate terpolymer is derived from either polyacrylic acid, polymethacrylic acid or polymaleic acid, and the sulfonate portion of the carboxylate-sulfonate copolymer or the carboxylate-sulfonate terpolymer is derived from an aliphatic or aromatic compound. The aliphatic compound comprises methacrylamido methyl propane sulfonic acid, and the aromatic compound comprises styrene sulfonic acid. The terpolymer incorporates a nonionic component such as (meth) acrylamide, substituted (meth)acrylamide, vinyl alcohol, allyl alcohol, vinyl esters, an ester of vinyl or allyl alcohol, styrene, isobutylene or diisobutylene.

The barrier film may be coated onto either the halogen donor or the PMPS composition. The barrier film may be coated by covering the composition with the barrier film material while mechanically mixing the barrier film material in a screw auger or a rotary drum. Alternatively, the barrier film may be applied by using a fluidized driver. If the barrier film material is an inorganic salt, it may be applied before, during, or after the drying of the composition. If the barrier film material is silicate, borosilicate, and/or organic polymer, on the other hand, it is preferably applied to the composition either while the composition is drying or after the composition is dried. The coating is then applied in the form of a foam or atomized spray to maximize distribution, and further dried by using a suitable conventional drier including but not limited to a rotary drier or a fluidized drier.

A halogen-PMPS product containing the PMPS composition and one or more of the halogen donors can effectively control the chloramine, COD, and TOC levels in the treated water and reduce or even eliminate the problems associated with the accumulation of these undesirable products. Further, the halogen-PMPS composition reduces or eliminates any byproducts resulting from incomplete oxidation of the waste. This composition may be in powder form, granular form, or in the shape of a pellet, nugget, tablet, sphere, briquette, puck, etc.

The halogen component functioning as the halogen oxidizer may be calcium hypochlorite, trichloroisocyanurate, dichloroisocyanurate, lithium hypochlorite, dibromo-dimethylhydantoin, bromo-chloro-dimethylhydantoin, sodium bromide, sodium chloride, or a combination thereof.

The PMPS compound used for the PMPS-halogen product has a $K_2S_2O_8$ byproduct concentration below 0.5 wt. % and preferably below 0.2 wt. %. The low $K_2S_2O_8$ concentration allows the PMPS-halogen product to be used at a higher dosage than what is currently allowed. In fact, the PMPS-halogen product may be used continually while the pool is being used.

The composition can then be shaped into a useful solid form by using established processing techniques. If the composition is granular, it may be produced using rotary mixers and/or rotary driers. Alternatively, a spray graining technique may be used with a fluidized drier. If the composition is a tablet, a nugget, a briquette, a sphere, a puck or a solid object of a different shape, it may be produced by combining and mixing the components of the composition and applying pressure to a mold or extruding the objects of the desired shape. Optionally, a well-known binding agent may be used to enhance the cohesiveness of the particles. The pressure level that is applied during extrusion may be adjusted according to the desired hardness of the end product.

The shaped composition (e.g., a tablet) is inserted into a feeder or a strainer at any location in the pool, or into a pool circulating system that is continuously or periodically immersed in the water to be treated. The PMPS-halogen product is preferably released in a controlled manner. Besides a tablet, some exemplary shapes for the PMPS-halogen product include powder, granules, nugget, briquette, pucks, etc.—anything deemed suitable by a person skilled in the art. The disclosed stable composition can then be employed in water treatment applications as an improved disinfectant.

The PMPS-halogen product may be used in a liquid form. To prepare the liquid form of PMPS-halogen product, the solid form of PMPS-halogen product is dissolved in water using any number of dry product feed devices. For example, a tank with a mixer and a pump may be used. Alternatively, a chemical feeder which contains the PMPS composition may be used to dissolve some or all of the composition before using the solution. Using the chemical feed, the composition may be applied by periodically using a timer, or by manually or automatically activating the feed system. The method allows for frequent incremental feed or continuous feed of the composition even when bathers are present, without concern of causing irritation. "Frequent incremental feed," as used herein, refers to a feed of at least one cycle per day.

When the PMPS-halogen composition is used to treat water that contains bathers' waste, the concentration of chloramines and other undesirable byproducts is sustained at much lower levels than when the components of the composition are used separately. Furthermore, when the pool water is "shock" treated by addition of the powder or granular composition across the surface of the pool, the combined level of chlorine and other undesirable contaminants is reduced to a level much lower than that achieved using current methods of shock treatment or breakpoint chlorination. Also, with the halogen-PMPS composition of the invention, there is no need for an oxidation reduction potential (ORP) control device of the type disclosed in U.S. Pat. No. 6,620,315.

Optionally, various other additives such as pH buffering agents, coagulants, clarifiers, algae control agents (e.g., boron or lanthanum based additives) may be included in the halogen-PMPS composition without deviating from the scope of this invention.

Although preferred embodiments of the present invention have been described in detail hereinabove, it should be clearly understood that many variations and/or modifications of the basic inventive concepts herein taught which may appear to those skilled in the present art will still fall within the spirit and scope of the present invention.

What is claimed is:

1. A water treatment composition for use while mammals are present, comprising:
   a potassium monopersulfate component including a triple salt of the formula $(KHSO_5)_x(KHSO4)_y(K_2SO4)_z$, wherein $x+y+z=1$, wherein said triple salt contains a $K_2S_2O_8$ byproduct and the concentration of said $K_2S_2O_8$ byproduct is less than 0.5 percent (%) by weight;
   a halogen component including a halogen donor compound selected from chlorine and bromine; and
   a barrier film, wherein the barrier turn includes an inorganic salt, silicate, borosilicate, an organic polymer, or a combination thereof.

2. The water treatment composition of claim 1, wherein the potassium monopersulfate component is about 4 to about 70.8 wt. % of the water treatment composition.

3. The water treatment composition of claim 1, wherein the halogen component is about 29 to about 95.8 wt. % of the water treatment composition.

4. The water treatment composition of claim 1, wherein the barrier film is about 0.2 to about 10 wt. % of the water treatment composition.

5. The water treatment composition of claim 1, wherein the potassium monopersulfate component is about 4 to about 70.8 wt. % of the water treatment composition, the halogen donor is about 29 to about 95.8 wt. % of the water treatment composition, and the barrier film is about 0.2 to about 10 wt. % of the water treatment composition.

6. The water treatment composition of claim 1, wherein $x=0.42–0.64$, $y=0.15–0.40$, and $z=0.15–0.40$.

7. The water treatment composition of claim 1, wherein $x=0.48–0.64$, $y=0.15–0.37$, and $z=0.15–0.37$.

8. The water treatment composition of claim 1, wherein the potassium monopersulfate component comprises:
   about 43 to about 76 wt. % $KHSO_5$;
   less than about 0.5 wt. % of $K_2S_2O_8$; and
   about 0.0 to abort 10 wt. % of alkali magnesium salt.

9. The water treatment composition of claim 7, wherein the fraction of $K_2S_2O_8$ is less than about 0.2 wt. %.

10. The water treatment composition of claim 8, wherein the alkali magnesium salt comprises one or more of $Mg(OH)_2$, $MgCO_3$, $Mg(HCO3)_2$, $MgO$, $(MgCO_3)4$-$Mg(OH)_2$-$5H_2O$, $CaMg(CO_3)_2$, $MgO$—$CaO$, $Ca(OH)_2$—$MgO$ or combinations thereof.

11. The water treatment composition of claim 1, wherein the halogen donor comprises one or more of calcium hypochlorite, trichloroisocyanurate, dichloroisocyanurate, lithium hypochlorite, dibromo-dimethylhydantoin, bromochloro-dimethylhydantoin, and a combination thereof.

12. The water treatment composition of claim 1, wherein the inorganic salt comprises sodium; carbonate, bicarbonate, hydroxide, oxide, silicate, borate, potassium; carbonate, bicarbonate, hydroxide, oxide, silicate, borate, magnesium; carbonate, bicarbonate, hydroxide, oxide, silicate, borate, calcium; carbonate, bicarbonate, hydroxide, oxide, silicate, borate, or a combination thereof.

13. The water treatment composition of claim 1 further comprising one or more of pH buffering agents, coagulant, clarifiers, and algae control agents.

14. The water treatment composition of claim 1, wherein the barrier film is deposited on one or both of the potassium monopersulfate component and the halogen donor.

15. A water treatment composition for use while mammals are present, comprising:
   a potassium monopersulfate component including a triple salt of the formula $(KHSO_5)_x(KHSO_4)_y(K_2SO_4)_z$, wherein x+y+z=1, wherein said triple salt contains a $K_2S_2O_8$ byproduct and the concentration of said $K_2S_2O_8$ byproduct is less than 0.5 percent (%) by weight;
   a halogen component including a halogen donor compound selected from chlorine and bromine and
   a barrier film, wherein the barrier film includes an inorganic silicate, borosilicate, an organic polymer, or a combination thereof, wherein the silicate comprises sodium, potassium, lithium, alkyl silicate, borosilicate, or a combination thereof.

16. A water treatment composition for use while mammals are present, comprising:
   a potassium monopersulfate component including a triple salt of the formula $(KHSO_5)_x(KHSO4)_y(K_2SO5)_z$ wherein x+y+z=1, wherein said triple salt contains a $K_2S_2O_8$ byproduct and the concentration of said $K_2S_2O_8$ byproduct is less than 0.5 percent (%) by weight;
   a halogen component including a halogen donor compound selected from chlorine and bromine; and
   a barrier film, wherein the baffler film includes a silicate, a borosilicate, an organic polymer or a combination thereof, wherein the organic polymer comprises chitin, chitosan, polymaleic avid, phosphinocarboxylic acid, carboxylate-sulfonate copolymer, a carboxylate-sulfonate terpolymer, or a combination thereof.

17. A water treatment composition for use while mammals are present, comprising:
   a potassium monopersulfate component including a triple salt of the formula $(KHSO_5)_x(KHSO_4)_y(K_2SO_5)_z$ wherein x+y+z=1;
   a halogen component including a halogen donor compound selected from chlorine and bromine; and
   a barrier film, wherein the baiter film is an organic polymer comprising a carboxylate-sulfonate copolymer or a carboxylate-sulfonate copolymer, wherein the carboxylate component of the carboxylate-sulfonate copolymer or the carboxylate-sulfonate terpolymer is derived from either polyacrylic acid, polymethacrylic acid or polymaleic acid.

18. The water treatment composition of claim 17, wherein the terpolymer incorporates a nonionic component such as (meth)acrylamide, substituted (meth)acrylamide, vinyl alcohol, allyl alcohol, vinyl esters, an ester of vinyl or allyl alcohol, styrene, isobutylene or diisobutylene.

19. A water treatment composition for use while mammals are present, comprising:
   a potassium monopersulfate component including a triple salt of the formula $(KHSO_5)_x(KHSO_4)_y(K_2SO_5)_z$ wherein x+y+z=1;
   a halogen component including a halogen donor compound selected from chlorine and bromine; and
   a barrier film, wherein the barrier film is an organic polymer comprising a carboxylate-sulfonate copolymer or a carboxylate-sulfonate copolymer, wherein the sulfonate portion of the carboxylate-sulfonate copolymer or the carboxylate-sulfonate terpolymer is derived from an aliphatic or aromatic compound.

20. The water treatment composition of claim 19, wherein the aliphatic compound comprises methacrylamido methyl propane sulfonic acid.

21. The water treatment composition of claim 19, wherein the aromatic compound comprises styrene sulfonic acid.

22. A method of combining potassium monopersulfate and a halogen donor compound selected from chlorine and bromine into a stable product for use while mammals are present, the method comprising:
   coating the potassium monopersulfate with one or more of inorganic salt, silicate, borosilicate, and organic polymer; and
   adding the halogen donor compound to the coated potassium monopersulfate to form a coagulated product, wherein said potassium monopersulfate component includes a triple salt of the formula $(KHSO_5)_x(KHSO_4)_y(K_2SO_4)_z$, wherein x+y+z=1, and said triple salt contains a $K_2S_2O_8$ byproduct at a concentration of less than 0.5 percent (%) by weight.

23. A method of preparing a water treatment composition for use while mammals are present, the method comprising:
   providing a potassium monopersulfate component;
   combining the potassium monopersulfate component with a halogen donor compound selected from chlorine and bromine and a barrier flint, wherein the barrier film includes an inorganic salt, silicate, borosilicate, an organic polymer, or a combination thereof, and said potassium monopersulfate component includes a triple salt of the formula $(KHSO_5)_x(KHSO_4)_y(K_2SO_4)_z$, wherein x+y+z=1, and said triple salt contains a $K_2S_2O_8$ byproduct at a concentration of less than 0.5 percent (%) by weight.

24. The method of claim 23 further comprising combining the potassium monopersulfate component wit the halogen donor and the barrier film such that the potassium monopersulfate component comprises about 4 to about 70.8 wt. % of the water treatment composition.

25. The method of claim 23 further comprising combining the potassium monopersulfate component with the halogen donor and the barrier film such that the halogen donor comprises about 29 to about 95.8 wt. % of the water treatment composition.

26. The method of claim 23 further comprising combining the potassium monopersulfate component with the halogen donor and the barrier film such that the barrier film comprises about 0.2 to about 10 wt. % of the water treatment composition.

27. The method of claim 23 further comprising combining the potassium monopersulfate component with the halogen donor and the barrier film such that the potassium monopersulfate component comprises about 4 to about 70.8 wt. % of the water treatment composition, the halogen donor comprises about 29 to about 95.8 wt. % of the water treatment composition, and the barrier film comprises about 0.2 to about 10 wt. % of the water treatment composition.

28. The method of claim 23, wherein preparing the potassium monopersulfate component comprises preparing a composition that is about 43 to about 76 wt. % KHSO5, and about 0.0 to about 10 wt. % of alkali magnesium salt.

29. The method of claim 28, wherein preparing the potassium monopersulfate component comprises preparing a composition that is about 43 to about 76 wt. % $KHSO_5$, less than about 0.2 wt. % of $K_2S_2O_8$, and about 0.0 to about 10 wt. % of alkali magnesium salt.

30. The method of claim 28, wherein the alkali magnesium salt comprises one or more of $Mg(OH)_2$, $MgCO_3$, $Mg(HCO_3)_2$, MgO, $(MgCO_3)4-Mg(OH)_2-5H_2O$, $CaMg(CO_3)_2$ MgO—CaO, $Ca(OH)_2$—MgO or combinations thereof.

31. The method of claim 23, wherein the halogen donor comprises one or more of calcium hypochlorite, trichloroisocyanurate, dichloroisocyanurate, lithium hypochlorite, dibromo-dimethylhydantoin, bromo-chloro-dimethylhydantoin, and a combination thereof.

32. The method of claim 23, wherein the inorganic salt comprises sodium; carbonate; bicarbonate, hydroxide, oxide, silicate, borate, potassium carbonate, bicarbonate, hydroxide, oxide, silicate, borate, magnesium; carbonate, bicarbonate, hydroxide, oxide, silicate, borate, calcium; carbonate, bicarbonate, hydroxide, oxide, silicate, borate, or a combination thereof.

33. The method of claim 23 further comprising depositing the barrier film on one or both of the potassium monopersulfate component and the halogen donor.

34. The method of claim 23 further comprising shaping the combination of potassium monopersulfate component, the halogen donor, and the barrier film into a solid product of preselected dimensions by using one or more of spray gaining, extruding, and molding.

35. The method of claim 23 further comprising adding one or more of pH buffering agents, coagulants, clarifiers, and algae control agents to the combination of potassium monopersulfate component the halogen donor, and the barrier film.

36. A method of preparing a water treatment composition for use while mammals are present, the method comprising:
providing a potassium monopersulfate component;
combining the potassium monopersulfate component with a halogen donor selected from chlorine and bromine and a barrier film, wherein the barrier film includes an inorganic salt silicate, borosilicate, an organic polymer, or a combination thereof wherein the potassium monopersulfate component and the halogen donor are combined such that a weight ratio of the halogen donor to the potassium monopersulfate component is between about 0.05 to about 20.

37. A method of combining potassium monopersulfate and a halogen donor selected from chlorine and bromine into a stable product for use while mammals are present, the method comprising:

coating the potassium monopersulfate with one or more of inorganic salt, silicate, borosilicate, and organic polymer, wherein the silicate comprises sodium, potassium, lithium, alkyl silicate, borosilicate, or a combination thereof; and
adding the halogen donor to the coated potassium monopersulfate to form a coagulated product, wherein said potassium monopersulfate component includes a triple salt of the formula $(KHSO_5)_x(KHSO_4)_y(K_2SO_4)_z$, wherein $x+y+z=1$, and said triple salt contains a $K_2S_2O_8$ byproduct at a concentration of less than 0.5 percent (%) by weight.

38. A method of preparing a water treatment composition for use while mammals are present the method comprising:
providing a potassium monopersulfate component;
combining the potassium monopersulfate component with a halogen donor compound selected from chlorine and bromine and a barrier film wherein the barrier film includes an inorganic salt, silicate, borosilicate, an organic polymer, or a combination thereof, wherein the organic polymer comprises chitin, chitosan, polymaleic acid, phosphinocarboxylic acid, carboxylate-sulfonate copolymer, a carboxylate-sulfonate terpolymer, or a combination thereof.

39. The method of claim 38, wherein the carboxylate component of the carboxylate-sulfonate copolymer or the carboxylate-sulfonate terpolymer is derived from either polyacrylic acid, polymethacrylic acid or polymaleic acid.

40. The method of claim 38, wherein the sulfonate portion of the carboxylate-sulfonate copolymer or the carboxylate-sulfonate terpolymer is derived from an aliphatic or aromatic compound.

41. The method of claim 40, wherein the aliphatic compound comprises methacrylamido methyl propane sulfonic acid.

42. The method of claim 40, wherein the aromatic compound comprises styrene sulfonic acid.

43. The method of claim 38, wherein the terpolymer incorporates a nonionic component such as (meth)acrylamide, substituted (meth)acrylamide, vinyl alcohol, allyl alcohol, vinyl esters, an ester of vinyl or allyl alcohol, styrene, isobutylene or diisobutylene.

44. A method of treating water, comprising:
obtaining a solid product containing potassium monopersulfate and a halogen donor compound selected from chlorine and bromine; and periodically adding the mixture to a body of water while mammals are present.

45. The method of claim 44 further comprising dissolving the solid product in water prior to adding.

46. A composition for combining potassium monopersulfate and a halogen donor compound selected from chlorine and bromine, the composition comprising one or more of an inorganic salt, a silicate, a borosilicate, and an organic polymer, wherein said potassium monopersulfate component includes a triple salt of the formula $(KHSO_5)_x(KHSO_4)_y(K_2SO_4)_z$, wherein $x+y+z=1$, and said triple salt contains a $K_2S_2O_8$ byproduct at a concentration of less than 0.5 percent (%) by weight.

* * * * *